United States Patent
Moran et al.

(12)

(10) Patent No.: US 10,725,047 B2
(45) Date of Patent: Jul. 28, 2020

(54) METHODS AND SYSTEMS FOR ANALYZING A BLOOD SAMPLE

(71) Applicant: GLUCOME LTD., Yarkona (IL)

(72) Inventors: Dov Moran, Kfar Saba (IL); Yiftah Ben Aharon, Moshav Bakoa (IL); Itay Cohen, Raanana (IL); Roee Tuval, Ramat Hasharon (IL)

(73) Assignee: GLUCOME, LTD., Yarkona (IL)

( * ) Notice: Subject to any disclaimer, the term of this patent is extended or adjusted under 35 U.S.C. 154(b) by 0 days.

(21) Appl. No.: 14/133,706

(22) Filed: Dec. 19, 2013

(65) Prior Publication Data
US 2014/0179013 A1    Jun. 26, 2014

Related U.S. Application Data (60) Provisional application No. 61/739,743, filed on Dec. 20, 2012, provisional application No. 61/885,523, filed on Oct. 2, 2013.

(51) Int. Cl.
   *G01N 27/327* (2006.01)
   *G01N 33/66* (2006.01)
   *G01N 33/487* (2006.01)

(52) U.S. Cl.
   CPC ....... *G01N 33/66* (2013.01); *G01N 33/48792* (2013.01); *Y10T 436/144444* (2015.01)

(58) Field of Classification Search
   CPC .................. G01N 33/66; G01N 33/48792
   USPC .......................... 436/95; 422/82.05; 205/782; 204/403.01
   See application file for complete search history.

(56) References Cited

U.S. PATENT DOCUMENTS

| | | | |
|---|---|---|---|
| 6,909,793 B1 | 6/2005 | Mori et al. | |
| 2001/0032098 A1* | 10/2001 | Kulkarni | ............ 705/2 |
| 2005/0273080 A1* | 12/2005 | Paul | .... G06F 19/3406 604/890.1 |
| 2007/0093717 A1* | 4/2007 | Nagar et al. | .......... 600/438 |

(Continued)

FOREIGN PATENT DOCUMENTS

EP    1757222 A1    2/2007

OTHER PUBLICATIONS

Huang, X. A Capacitive MEMS Viscometric Sensor for Affinity Detection of Glucose. Journal of Microelectromechanical Systems. (2009) 1246-1254.20100169035.*

*Primary Examiner* — Rebecca M Fritchman
(74) *Attorney, Agent, or Firm* — Alphapatent Associates, Ltd.; Daniel J. Swirsky (57) ABSTRACT

A method of analyzing a blood sample is provided. The method comprises providing a glucometer configured to analyze a blood sample and a remote computing device separate from the glucometer, analyzing, by the glucometer, the blood sample, and presenting, by the glucometer, encoded results. The encoded results may be presented as a machine-readable visually-encoded representation of one or more results of the analysis, in which case the method further comprises imaging, by the remote computing device, the representation. The encoded results may be presented as a capacitive profile, in which case the method further comprises reading, by a capacitive sensing input mechanism of the remote computing device, the capacitive profile. According to either option, the method further comprises decoding, by the remote computing device, the representation, thereby retrieving at least one of the results.

7 Claims, 4 Drawing Sheets

(56) References Cited

U.S. PATENT DOCUMENTS

| | | | |
|---|---|---|---|
| 2010/0169035 A1* | 7/2010 | Liang | A61B 5/14865 |
| | | | 702/65 |
| 2011/0224564 A1* | 9/2011 | Moon et al. | 600/509 |
| 2012/0266251 A1 | 10/2012 | Birtwhistle et al. | |
| 2013/0032634 A1* | 2/2013 | McKirdy | G06Q 30/0271 |
| | | | 235/375 |
| 2013/0076533 A1 | 3/2013 | Moran | |
| 2013/0346008 A1* | 12/2013 | Bulea | 702/85 |

* cited by examiner

METHODS AND SYSTEMS FOR ANALYZING A BLOOD SAMPLE

CROSS-REFERENCE TO RELATED APPLICATIONS

This application claims the benefit of priority from U.S. Provisional Patent Application No. 61/739,743, filed Dec. 20, 2012, and U.S. Provisional Patent Application No. 61/885,523, filed Oct. 2, 2013, the contents of which are incorporated herein by reference in their entirety.

FIELD OF THE INVENTION

The disclosure herein relates to the methods and systems for analyzing the glucose level of a blood sample. In particular, it relates to methods and systems for transmitting information between elements of the system.

BACKGROUND OF THE INVENTION

Diabetes is a metabolic disease characterized by high blood sugar, also called glucose, resulting from disruption in production of, or lack of proper response to, insulin, a hormone central to regulating carbohydrate and fat metabolism.

More than 18.2 million people (or 6.3 percent of the population) in the United States suffer from diabetes. Diabetes can cause serious health complications including heart disease, blindness, kidney failure, and lower-extremity amputations. These complications may be avoided through effective and efficient balance of sugar levels. The glucometers (also called a glucose meter) is one tool for reaching and maintaining an optimal balance of blood sugar.

Many glucometers use an electrochemical method, based on test media such as test strips. Test strips are a consumable element containing chemicals that react with glucose in a drop of blood used for each measurement. The test media are typically single-use elements which are sold in packages which must be replaced once they are all used.

SUMMARY OF THE INVENTION

According to one aspect of the presently disclosed subject matter, there is provided a method of analyzing a blood sample, the method comprising:
providing a glucometer configured to analyze a blood sample and a remote computing device separate from the glucometer;
analyzing, by the glucometer, the blood sample;
presenting, by the glucometer, a machine-readable visually-encoded representation of one or more results of the analysis;
imaging, by the remote computing device, the representation; and
decoding, by the remote computing device, the representation, thereby retrieving at least one of the results.

The visually encoded representation may comprise a pattern. The pattern may be selected from the group including one-dimensional and two-dimensional barcodes. The pattern may comprise alphanumeric characters.

The visually encoded representation may comprise a sequence of visual elements. The glucometer may comprise one or more LEDs, the visual elements being one or more flashes of the LEDs. The LEDs may be multi-color, wherein different colors of each LED represent different values of encoded data.

The method may further comprise presenting machine-readable visually-encoded representation of at least one of error-correction and error-detection information.

According to another aspect of the presently disclosed subject matter, there is provided a method of analyzing a blood sample, the method comprising:
providing a glucometer configured to analyze a blood sample and comprising a capacitive profile output mechanism;
providing a remote computing device separate from the glucometer and comprising a capacitive sensing input mechanism;
analyzing, by the glucometer, the blood sample;
encoding, by the glucometer, one or more results of the analysis as a capacitive profile;
producing, by the capacitive profile output mechanism, the capacitive profile;
reading, by the capacitive sensing input mechanism, the capacitive profile; and
decoding, by the remote computing device, the capacitive profile, thereby retrieving at least one of the results.

The capacitive profile may comprise a sequence of capacitive states varying over a period of time.

The capacitive profile may comprise a plurality of regions, each exhibiting a capacitive state.

Each region may exhibit a sequence of capacitive states varying over a period of time.

The capacitive profile may further comprise at least one of error-correction and error-detection information.

According to a further aspect of the presently disclosed subject matter, there is provided a glucometer comprising:
a reader configured to analyze a blood sample;
a processor configured to encode results of the analysis; and
a capacitive output mechanism configured to represent the encoded results.

The capacitive output mechanism may be configured to exhibit a sequence of capacitive states varying over a period of time.

The capacitive output mechanism may comprise a plurality of regions, each region being configured to exhibit a capacitive state independent of the other regions. The glucometer may be being configured to exhibit a sequence of capacitive states in each region varying over a period of time.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice. In the accompanying drawings.

DETAILED DESCRIPTION OF THE INVENTION

Figure 1:
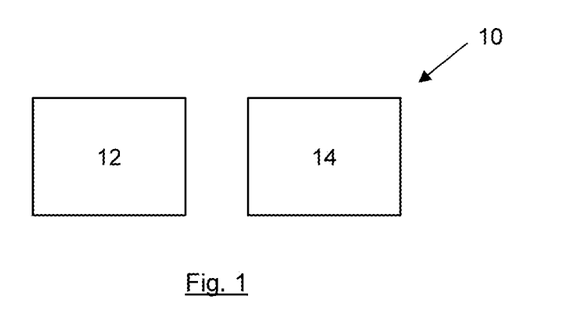
FIG. 1 is a schematic illustration of a system according to one example of the presently disclosed subject matter.

According to one example, as illustrated schematically in FIG. 1, there is provided a system, which is generally indicated at 10, for measuring the glucose level of a user. The system 10 comprises a glucometer 12 and a remote computing device 14.

Figure 2:
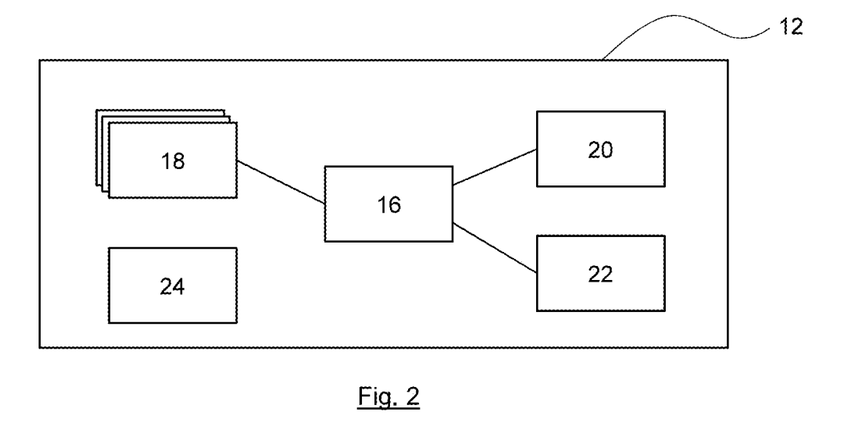
FIG. 2 is a schematic illustration of a glucometer of the system illustrated in FIG. 1.

As illustrated schematically in FIG. 2, the glucometer 12 comprises a processor 16, one or more memory modules 18 (which may comprise volatile and/or non-volatile memory), a media reader 20, a visual display 22, and a power source 24. In addition, it may optionally comprise other elements (not illustrated), such as an external memory reader, a transmitter, one or more ports configured for connection to a data cable, etc.

The media reader 20 is configured to facilitate analyzing a blood sample disposed on a test media (not illustrated), such as a test strip, disc, drum, cartridge, or any other suitable medium. It may be designed so as to facilitate detecting the glucose level in the blood sample using any suitable method. For example, in an electrochemical method, the blood sample reacts with one or more chemicals impregnated on the test medium. The amount of products of the reaction is proportional to the glucose level in the blood, and can be measured electrically by the media reader 20. Alternatively, the media reader 20 may operate using a coulometric or amperometric method, as is known in the art.

In addition, the media reader 20 may be configured to read information encoded on the test medium, including, but not limited to, calibration information, information regarding the make and/or model of the test medium, and information regarding the manufacturing of the test medium (such as batch number, manufacture date, expiration date, etc.).

The processor 16 is configured to direct operation of the elements of the glucometer 12. As such, it may be configured to facilitate analysis of the blood sample, encode information measured by the media reader 20 for display by, and direct operation of, the visual display 22, etc. In performing these tasks, it may utilize the one or more memory modules 18 for short-term storage of information.

The visual display 22 comprises one or more elements configured to visually present encoded data. It may comprise, e.g., one or more LEDs (for example multi-color LEDs, i.e., being configured to selectively produce light of different colors), a screen, such as LCD, LED, OLED, plasma display, ELD, electronic paper, or electronic ink, or any other suitable display elements. In addition, it may comprise a combination of two or more different display technologies.

As mentioned, the processor 16 is configured to facilitate displaying of encoded information regarding the results of the analysis by the visual display 22. The encoding may be accomplished by any suitable method. The method of displaying of the encoded results is dependent on the type of visual display 22.

The results may be encoded as a sequence of visual elements. For example, according to a modification wherein the visual display 22 comprises one or more LEDs, the information may be encoded and displayed as a time sequence of on/off states of the LEDs. In addition, different colors may be used to encode values of data. (For example, a multi-color LED may encode two bits of binary data in a single flash thereof, wherein each of four different colors indicates one of 00, 01, 10, and 11.) In addition, different durations of a flash may indicate different values. Combinations of the above may be employed, wherein the value transmitted by an LED depends both on the color and duration of its flash. According to some modifications, the visual display 22 comprises several LEDs, wherein the processor 16 is configured to transmit data separately via each LED simultaneously, jointly using all LEDS as a single data channel, or in combinations thereof.

Figure 3A:
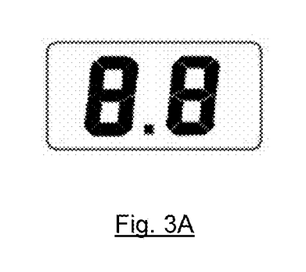
FIG. 3A illustrates an example of information encoded as alphanumeric characters.
Figure 3B:
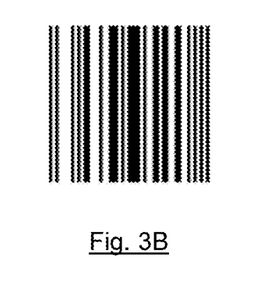
FIGS. 3B and 3C illustrate, respectively, examples of one-dimensional and two-dimensional barcodes.
Figure 3C:
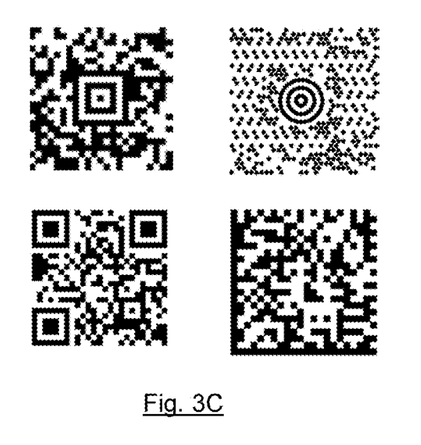

The results may be encoded as a pattern. For example, according to a modification wherein the visual display 22 comprises a screen, the processor 16 is configured to encode the information and direct the visual display 22 to present it as alphanumeric characters, for example as illustrated in FIG. 3A. According to other modifications, the processor 16 is configured to encode the information and direct the visual display 22 to present it as a barcode, e.g., as a one-dimensional barcode (an example of which is illustrated in FIG. 3B) or a two-dimensional barcode (examples of which are illustrated in FIG. 3C). It will be appreciated that if the visual display 22 is a color display, information may be encoded using different colors to indicate different values of encoded data.

In addition to information relating to the results of the analysis, the visual display 22 may present error-detection and/or error-correction information, e.g., as is well-known in the art.

The remote computing device 14 is any suitable device configured to receive information transmitted by the visual display 22 of the glucometer 12, execute a program, display information to a user, and optionally receive commands from a user. It may also be configured to communicate with an external network, for example a public network such as the Internet, a POTS network, an ISDN network, cellular telephone system, and/or a VoIP system. As such, it may be any computing device, such as a mobile phone built on a mobile operating system (also referred to as a "smartphone"), a tablet computer, a desktop or laptop computer, or any other suitable device. In particular, the remote computing device 14 is configured for installation thereon of third-party software.

Figure 4:
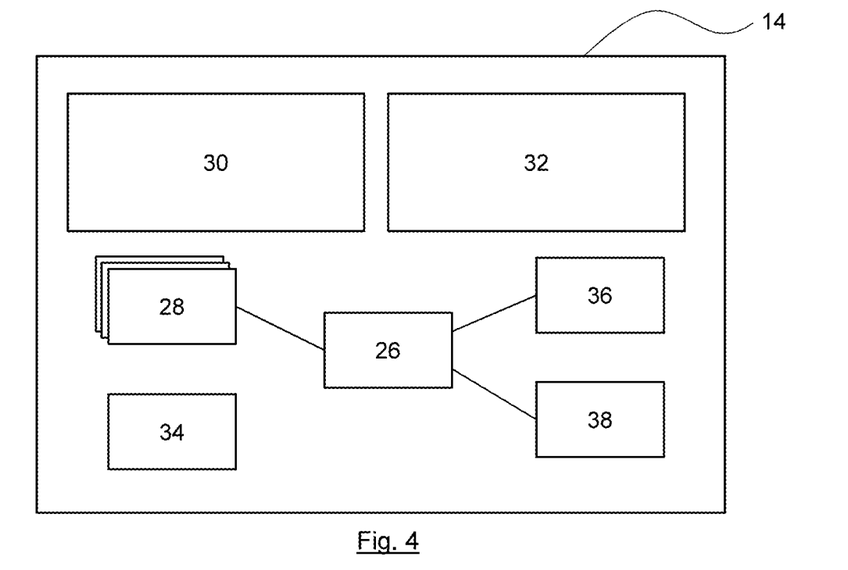
FIG. 4 is a schematic illustration of a remote computing device of the system illustrated in FIG. 1.

As illustrated schematically in the FIG. 4, the remote computing device 14 comprises a processor 26, one or more memory modules 28 (which may comprise volatile and/or non-volatile memory), a user-input interface 30, a user-output interface 32, a power source 34, and an imaging device 36. The user-input interface 30 and user-output interface 32 may be part of the same element, e.g., a touch-screen may constitute both.

In addition, the remote computing device 14 may comprise a transceiver 38, such as a modem and/or a wireless network adapter, configured to communicate with the external network.

The processor 26 is configured to direct operation of the remote computing device 14. Inter alia, it is configured to execute software stored in the memory modules 28. In addition, the processor 26 may be configured to facilitate updating software stored in the memory modules 28, for example by downloading updated software from a remote server via the Internet.

The imaging device 36 may be any suitable device for digitally capturing an image, for example a digital camera integrated into a smartphone or tablet computer, or a digital still or video camera in communication with a desktop or laptop computer (such as a webcam). The processor 26 is configured to analyze an image captured by the imaging device 36. In particular, it is configured to analyze the image to establish whether is contains encoded data, and to decode the data. The remote computing device 14 may be loaded with a software application which is configured to facilitate the decoding. For example, the information transmitted by the glucometer 12 may contain raw data obtained by the media reader 20, which the software application is configured to interpret and provide a useful value based thereon. It may further be provided to track glucose levels over time, communicate with one or more outside servers, etc.

The system 10 as described above may be configured to monitor and/or track usage of test media by the glucometer 12. Software configured to perform the tracking may be installed in the memory of either the glucometer 12 or the remote computing device 14. Alternatively, the glucometer 12 and remote computing device 14 may each be loaded with complementary software which together perform this task.

Figure 5:
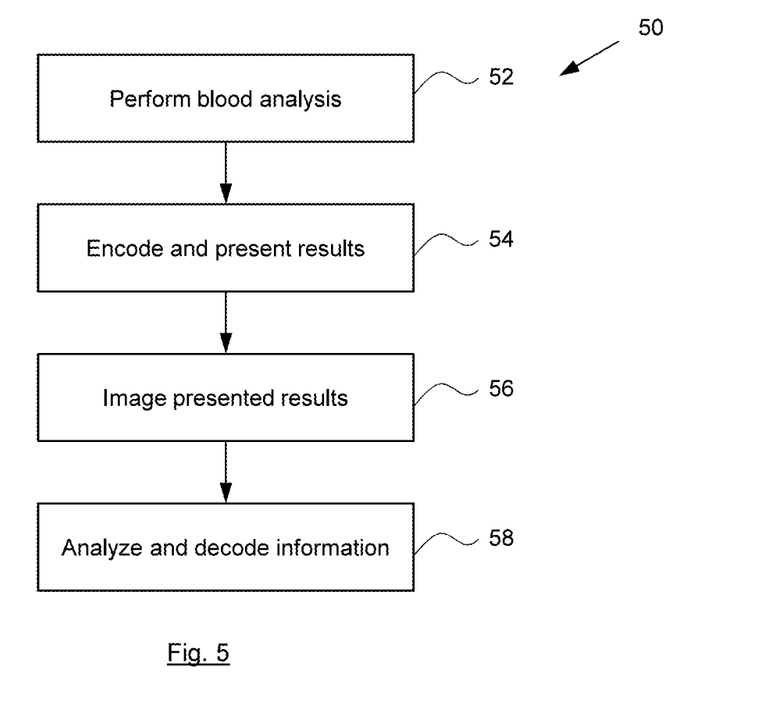
FIG. 5 illustrates a method for transmitting results of an analysis performed by the glucometer illustrated in FIG. 2 to the remote computing device illustrated in FIG. 4.

As illustrated in FIG. 5, the system 10, e.g., by running appropriate software (either installed on one of its constituent devices, or as complementary software on both), is configured to execute a method, which is generally indicated at 50, for transmitting information from the glucometer 12 to the remote computing device 14.

In step 52, a user utilizes the glucometer 12 to perform a blood analysis. This may be performed according to any suitable method known in the art.

In step 54, the processor 16 encodes the results of the analysis as a visual pattern, for example as described above in connection with FIGS. 2 through 3C, and presents the encoded results via the visual display 22 of the glucometer 12.

In step 56, the remote computing device 14 is used to image the encoded results presented by the visual display 22 in step 54, for example using the imaging device 36. According to some modifications, the remote computing device 14 receives an image of the encoded results presented by the visual display 22 via a third-party device, e.g., a user of the glucometer 12 may capture an image of the visual display 22 and send it electronically to the remote computing device 14.

In step 58, the processor 26 of the remote computing device 14 analyzes the captured image. If it determines that the image comprises encoded data, it decodes the information. The remote computing device 14 may take any suitable predetermined action, e.g., presenting the decoded information via the user-output interface 32, storing it, performing calculations based thereon, making one or more recommendations to the user based thereon, transmitting it to a third-party (for example via the transceiver 38) such as a medical professional or an Internet-based storage system, etc.

Figure 6:
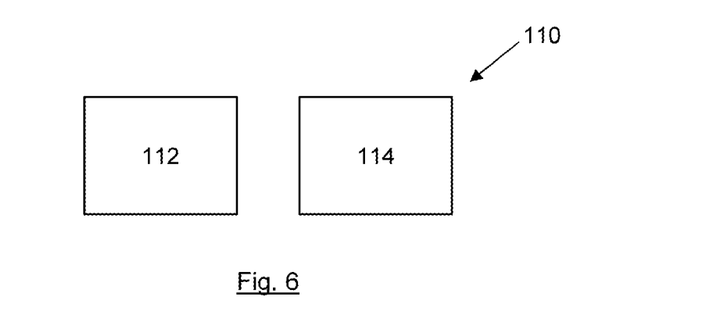
FIG. 6 is a schematic illustration of a system according to another example of the presently disclosed subject matter.

According to another example, as illustrated schematically in FIG. 6, there is provided a system, which is generally indicated at 110, for measuring the glucose level of a user. The system 110 comprises a glucometer 112 and a remote computing device 114.

Figure 7:
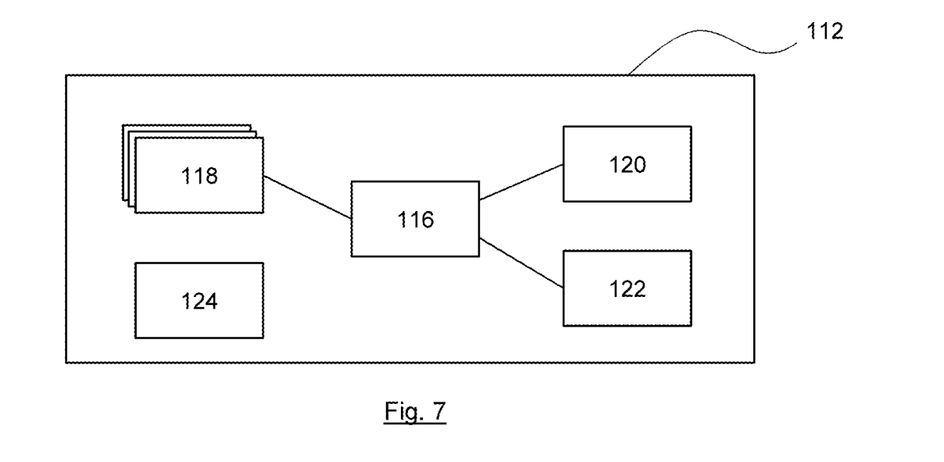
FIG. 7 is a schematic illustration of a glucometer of the system illustrated in FIG. 6.

As illustrated schematically in FIG. 7, the glucometer 112 comprises a processor 116, one or more memory modules 118 (which may comprise volatile and/or non-volatile memory), a media reader 120, a capacitance output mechanism 122, and a power source 124. In addition, it may optionally comprise other elements (not illustrated), such as an external memory reader, a visual display, a transmitter, one or more ports configured for connection to a data cable, etc.

The media reader 120 is configured to facilitate analyzing a blood sample disposed on a test media (not illustrated), such as a test strip, disc, drum, cartridge, or any other suitable medium. It may be designed to facilitate detecting the glucose level in the blood sample using any suitable method. For example, in an electrochemical method, the blood sample reacts with one or more chemicals impregnated on the test medium. The amount of products of the reaction is proportional to the glucose level in the blood, and can be measured electrically by the media reader 120. Alternatively, the media reader 120 may operate using a coulometric or amperometric method, as is known in the art.

In addition, the media reader 120 may be configured to read information encoded on the test medium, including, but not limited to, calibration information, information regarding the make and/or model of the test medium, and information regarding the manufacturing of the test medium (such as batch number, manufacture date, expiration date, etc.).

The processor 116 is configured to direct operation of the elements of the glucometer 112. As such, it may be configured to facilitate analysis of blood sample, encode information measured by the media reader 120 for representation via, and direct operation of, the capacitive output mechanism 122, etc. In performing these tasks, it may utilize the one or more memory modules 118 for short-term storage of information.

The capacitive output mechanism 122 is configured to produce a capacitive profile, i.e., a pattern of capacitive states. The capacitive profile may be time-based, wherein the capacitive output mechanism 122 exhibits a sequence of varying capacitive states (i.e., levels of electrical charge storage capacity) over a period of time, for example changing between exhibiting no electrical charge storage capacity and a non-zero value of electrical charge storage capacity. Alternatively, as will be described below, the capacitive profile may be location-based. In addition, the capacitive profile may be a combination of location- and time-based. According to any example, the capacitive profile may include error-detection and/or error-correction information, e.g., as is well-known in the art.

Figure 8A:
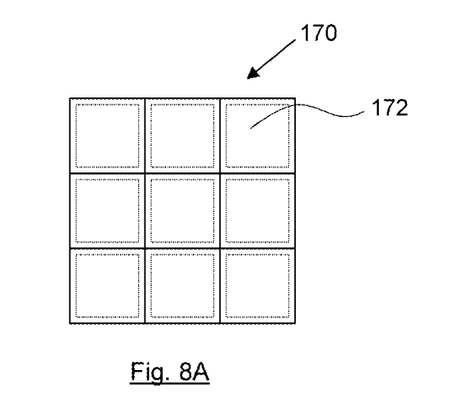
FIGS. 8A and 8B are, respectively, schematic plan and side views of a surface of a capacitive output mechanism of the glucometer illustrated in FIG. 7.
Figure 8B:
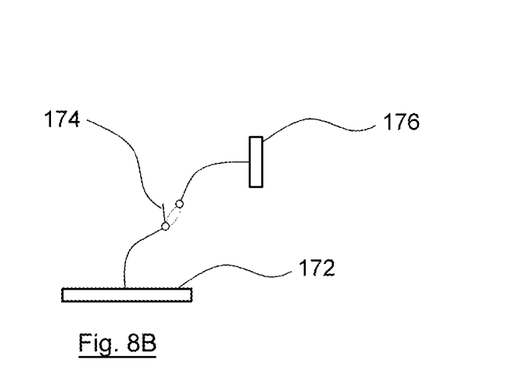

An example of a surface 170 of the capacitive output mechanism 122 which is configured for producing a location-based capacitive profile is illustrated in FIGS. 8A and 8B. The surface 170 is defined by nine regions 172 (only one of which is shown in profile in FIG. 8B), each being electrically connected on a back side thereof to a switch 174, which is configured to selectively toggle its respective region between connected and disconnected states with electrical charged conductance source 176. The source 176 may be electronics-based. Alternatively, it may be a surface of the glucometer 112 which is positioned so as to be in contact with a user's hand while in use, thereby taking advantage of the natural electrical charge conductance of the user. The processor 116 is configured to control each of the switches 174 such that its respective region 172 displays the proper capacitive state (i.e., electrical charge storage capacity), e.g., at the proper time.

As mentioned, the processor 116 is configured to facilitate representation of encoded information regarding the results of the analysis via the capacitive output mechanism 122. This representation is accomplished by controlling the capacitive profile.

According to modifications wherein the capacitive profile is time-based, the duration of time for which the capacitive output mechanism exhibits, e.g., a non-zero value of electrical charge storage capacity, may represent a certain value. For example, a predetermined interval of non-zero electrical charge storage capacity may represent the binary digit 1, while the same interval of no electrical charge storage capacity may represent the binary digit 0.

According to modifications wherein the capacitive profile is location-based, each region 172 may represent a predetermined bit in a binary string. One or more of the regions 172 may be utilized to indicate the orientation of the surface 170, for example by rapidly toggling its capacitive state in a predetermined fashion.

According to modifications wherein the capacitive profile is a combination of location- and time-based, each region 172 may produce a time-based capacitive profile independent of the other regions. In this way, multiple time-based capacitive profiles may be produces simultaneously, increasing the rate at which encoded information is represented via the capacitive output mechanism 122. One or more of the regions 172 may be utilized to indicate the orientation of the surface 170, for example by rapidly toggling its capacitive state in a predetermined fashion.

Figure 9:
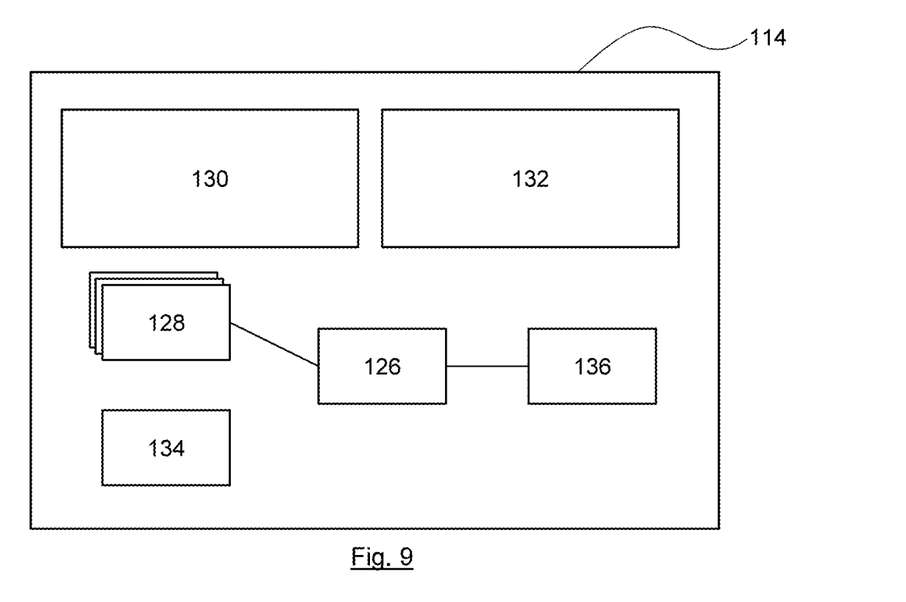
FIG. 9 is a schematic illustration of a remote computing device of the system illustrated in FIG. 6.

As illustrated schematically in the FIG. 9, the remote computing device 114 comprises a processor 126, one or more memory modules 128 (which may comprise volatile and/or non-volatile memory), a capacitive sensing user-input interface 130, a user-output interface 132, and a power source 134. The capacitive user-input interface 130 and user-output interface 132 may be part of the same element, e.g., a capacitive touch-screen may constitute both. According to some modifications, the capacitive user-input interface 130 may use multi-touch technology, i.e., it is configured to detect capacitive input at several locations simultaneously.

In addition, the remote computing device 114 may comprise a transceiver 136, such as a modem and/or a wireless network adapter, configured to communicate with the external network.

The processor 126 is configured to direct operation of the remote computing device 114. Inter alia, it is configured to execute software stored in the memory modules 128. In addition, the processor 126 may be configured to facilitate updating software stored in the memory modules 128, for example by downloading updated software from a remote server via the Internet.

In particular, the processor 126 is configured to analyze a capacitive profile captured by the capacitive user-input interface 130. It is configured to analyze the detected capacitive profile to establish whether is contains encoded data, and to decode the data. The remote computing device 114 may be loaded with a software application which is configured to facilitate the decoding. For example, the information transmitted by the glucometer 112 may contain raw data obtained by the media reader 120, which the software application is configured to interpret and provide a useful value based thereon. It may further be provided to track glucose levels over time, communicate with one or more outside servers, etc.

The system 110 as described above may be configured to monitor and/or track usage of test media by the glucometer 112. Software configured to perform the tracking may be installed in the memory of either the glucometer 112 or the remote computing device 114. Alternatively, the glucometer 112 and remote computing device 114 may each be loaded with complementary software which together perform this task.

Figure 10:
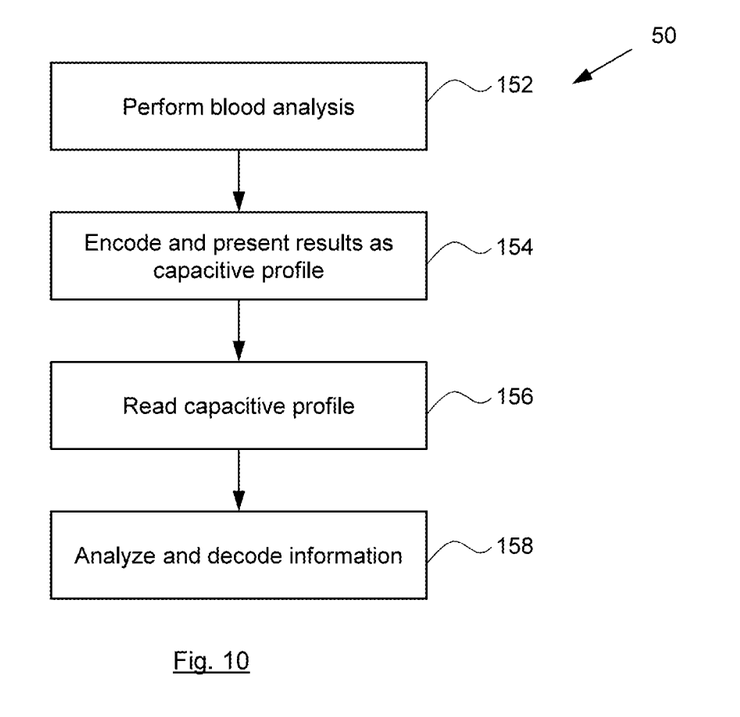
FIG. 10 illustrates a method for transmitting results of an analysis performed by the glucometer illustrated in FIG. 6 to the remote computing device illustrated in FIG. 9.

As illustrated in FIG. 10, the system 110, e.g., by running appropriate software (either installed on one of its constituent devices, or as complementary software on both), is configured to execute a method, which is generally indicated at 150, for transmitting information from the glucometer 112 to the remote computing device 114.

In step 152, a user utilizes the glucometer 112 to perform a blood analysis. This may be performed according to any suitable method known in the art.

In step 154, the processor 116 encodes the results of the analysis as a capacitive profile, for example as described above in connection with FIGS. 8A and 8B, and presents the encoded results via the capacitive output mechanism 122 of the glucometer 112.

In step 156, the capacitive sensing user-interface 130 of the remote computing device 114 reads the capacitive profile. This is accomplished by bringing the surface 170 of the capacitive output mechanism 122 of the glucometer 112 into contact with the capacitive sensing user-input interface 130. The processor 126 detects the encoded results presented via the capacitive output mechanism 122, thereby receiving the capacitive profile. In receiving the capacitive profile, the processor 126 may expect a predetermined orientation of the surface 170 of the capacitive output mechanism 122. Alternatively, the capacitive profile may include information indicating its orientation, for example as described above. The processor 126 may be configured to present, via the user-output interface 132, messages related to the contacting, for example that the orientation was invalid, that the contact was incomplete, that the capacitive profile was correctly received, etc.

In step 158, the processor 126 of the remote computing device 114 analyzes the detected capacitive profile. If it determines that the image comprises encoded data, it decodes the information. The remote computing device 114 may take any suitable predetermined action, e.g., presenting the decoded information via the user-output interface 134, storing it, performing calculations based thereon, making one or more recommendations to the user based thereon, transmitting it to a third-party (for example via the transceiver 136) such as a medical professional or an Internet-based storage system, etc.

Those skilled in the art to which this invention pertains will readily appreciate that numerous changes, variations and modifications can be made without departing from the scope of the invention mutatis mutandis.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the disclosure.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. A method of analyzing a blood sample, the method comprising:

providing a glucometer configured to analyze a blood sample and comprising (i) a capacitive profile output mechanism comprising circuitry for connecting and disconnecting at least one region of a surface of the glucometer with an electric capacitive source of the glucometer, thereby generating capacitive profiles at the at least one region of the surface of the glucometer, and (ii) a first processor configured to instruct the capacitive profile output mechanism to selectively connect and disconnect said at least one region with the electric capacitive source, each capacitive profile of said capacitive profiles comprising a pattern of capacitive states;

providing a computing device separate from the glucometer and comprising (i) a memory module, (ii) a second processor, and (iii) a capacitive sensing input mechanism, said capacitive sensing input mechanism comprising circuitry for sensing capacitance of the surface of the glucometer, thereby reading the capacitive profiles generated at the surface of the glucometer, said memory module storing software code and said second processor configured to decode said capacitive profiles by executing said software code;

analyzing, by the glucometer, the blood sample; and communicating one or more results of the analysis from the glucometer to the computing device, wherein the communicating comprises the steps of:

generating, by said first processor of the glucometer, at least one capacitive profile representing said results;

producing, by the capacitive profile output mechanism, the at least one capacitive profile representing said results by connecting and disconnecting said at least one region of said surface of the glucometer with said electric capacitive source;

bringing said computing device into contact with said glucometer such that said at least one capacitive profile produced by said capacitive profile output mechanism of the glucometer is detectable by said capacitive sensing input mechanism of the computing device;

while said computing device is in contact with said glucometer, reading, by the capacitive sensing input mechanism, said at least one capacitive profile representing said results by sensing capacitance of said surface of the glucometer; and executing software code stored on said memory module by said second processor, to decode said at least one capacitive profile representing said results, thereby retrieving at least one of the results.

2. The method according to claim 1, wherein the at least one capacitive profile comprises a sequence of capacitive states varying over a period of time.

3. The method according to claim 1, wherein the at least one capacitive profile comprises a plurality of regions, each exhibiting a capacitive state.

4. The method according to claim 3, wherein each region exhibits a sequence of capacitive states varying over a period of time.

5. The method according to claim 1, wherein the at least one capacitive profile further comprises at least one of error-correction and error-detection information.

6. The method of claim 1 wherein said capacitive source is electronics based.

7. The method of claim 1 wherein said capacitive source is a surface which is positioned so as to be in contact with a user's hand while in use.

\* \* \* \* \*